US010420944B2

(12) United States Patent
Tass et al.

(10) Patent No.: US 10,420,944 B2
(45) Date of Patent: Sep. 24, 2019

(54) DEVICE AND METHOD FOR EFFECTIVE INVASIVE NEUROSTIMULATION BY MEANS OF VARYING STIMULUS SEQUENCES

(71) Applicant: Forschungszentrum Juelich GmbH, Juelich (DE)

(72) Inventors: Peter Alexander Tass, Juelich (DE); Magteld Zeitler, Malden (NL)

(73) Assignee: FORSCHUNGSZENTRUM JUELICH GMBH, Juelich (DE)

( * ) Notice: Subject to any disclaimer, the term of this patent is extended or adjusted under 35 U.S.C. 154(b) by 165 days.

(21) Appl. No.: 15/528,606

(22) PCT Filed: Nov. 26, 2015

(86) PCT No.: PCT/EP2015/077797
§ 371 (c)(1),
(2) Date: May 22, 2017

(87) PCT Pub. No.: WO2016/083516
PCT Pub. Date: Jun. 2, 2016

(65) Prior Publication Data
US 2017/0259068 A1    Sep. 14, 2017

(30) Foreign Application Priority Data
Nov. 27, 2014  (DE) .................. 10 2014 117 429

(51) Int. Cl.
*A61N 1/36*  (2006.01)
*A61N 1/05*  (2006.01)
*A61N 5/06*  (2006.01)

(52) U.S. Cl.
CPC ....... *A61N 1/36185* (2013.01); *A61N 1/0531* (2013.01); *A61N 1/0534* (2013.01);
(Continued)

(58) Field of Classification Search
CPC .............. A61N 1/36185; A61N 1/0531; A61N 1/0534; A61N 1/36064; A61N 1/36067;
(Continued)

(56) References Cited

U.S. PATENT DOCUMENTS

| 7,228,179 | B2 * | 6/2007 | Campen ............ A61B 17/3468 607/46 |
| 2006/0069415 | A1 * | 3/2006 | Cameron et al. .. A61N 1/36146 607/45 |
| 2015/0018898 | A1 * | 1/2015 | Tass ................... A61N 1/36064 607/62 |

FOREIGN PATENT DOCUMENTS

| DE | 102010016461 A1 * | 10/2011 | .............. A61N 1/361 |
| DE | 102012002437 A1 * | 8/2013 | ......... A61N 1/36064 |

OTHER PUBLICATIONS

Adamchic, I., et al. (2014), Coordinated reset neuromodulation for Parkinson's disease: Proof-of-concept study. Mov Disord., 29: 1679-1684. doi:10.1002/mds.25923 (Year: 2014).*
(Continued)

*Primary Examiner* — Lindsey G Wehrheim
(74) *Attorney, Agent, or Firm* — Lowe Graham Jones PLLC; Bruce E. Black

(57) ABSTRACT

A device is provided for stimulating neurons that includes an implantable stimulation unit that generates stimuli in multiple stimulation elements. The stimulation unit generates the stimuli to stimulate a neuron population in the brain and/or spinal cord of a patient using the stimulation elements. Moreover, the device includes a control unit that controls the stimulation unit to repeatedly generates sequences of the stimuli with the order of the stimulation elements in which stimuli are generated within a sequence being constant for 20 or more successively generated sequences before it is varied.

20 Claims, 5 Drawing Sheets

(52) U.S. Cl.
CPC ..... *A61N 1/36064* (2013.01); *A61N 1/36067* (2013.01); *A61N 1/36075* (2013.01); *A61N 1/36082* (2013.01); *A61N 1/36103* (2013.01); *A61N 1/36175* (2013.01); *A61N 1/36178* (2013.01); *A61N 5/0622* (2013.01); *A61N 1/36021* (2013.01); *A61N 1/36071* (2013.01)

(58) Field of Classification Search
CPC ............ A61N 1/36075; A61N 1/36082; A61N 1/36103; A61N 1/36175; A61N 1/36178; A61N 1/36021; A61N 1/36071; A61N 5/0522
See application file for complete search history.

(56) References Cited

OTHER PUBLICATIONS

Tass, P. A., et al. (2012), Coordinated reset has sustained aftereffects in Parkinsonian monkeys. Ann Neurol., 72: 816-820. (Year: 2012).*
P. Temperli, et al. (2003), How do parkinsonian signs return after discontinuation of subthalamic DBS?. Neurology, 60 (1) 78-81; DOI: 10.1212/WNL.60.1.78 (Year: 2003).*
International Search Report for PCT/EP2015/077797 dated Jun. 1, 2017. (Year: 2017).*

* cited by examiner

DEVICE AND METHOD FOR EFFECTIVE INVASIVE NEUROSTIMULATION BY MEANS OF VARYING STIMULUS SEQUENCES

CROSS-REFERENCE TO RELATED APPLICATIONS

This application is a National Stage entry of International Application No. PCT/EP2015/077797, filed on Nov. 26, 2015, which claims priority to German Application No. 10 2014 117 429.1, filed on Nov. 27, 2014, the contents of each of these priority applications are hereby incorporated by reference in their entirety.

TECHNICAL FIELD

The invention relates to an apparatus and to a method for effective invasive neurostimulation by means of varying stimulus sequences.

BACKGROUND

Nerve cell assemblies in circumscribed regions of the brain, e.g. of the thalamus and the basal ganglia, are pathologically, e.g. excessively synchronously, active in patients with neurological or psychiatric diseases such as Parkinson's disease, essential tremor, epilepsy, functional disturbances after a stroke, dystonia or obsessive compulsive disorders. In this case, a large number of neurons synchronously form action potentials, i.e. the participating neurons fire excessively synchronously. In a healthy person, in contrast, the neurons fire with a different quality, e.g. in an uncorrelated manner, in these brain sectors.

In Parkinson's disease, the pathologically synchronous activity changes the neuronal activity in other brain regions, e.g. in areas of the cerebral cortex such as the primary motor cortex. In this respect, the pathologically synchronous activity in the region of the thalamus and of the basal ganglia, for example, imposes its rhythm on the cerebral cortex areas such that ultimately the muscles controlled by these areas develop pathological activity, e.g. a rhythmic trembling (tremor).

Deep brain stimulation is used to treat Parkinson's patients who cannot be sufficiently treated by medication. In this process, deep electrodes are implanted in specific areas of the brain, e.g. in the subthalamic nucleus. An electrical stimulation is carried out via the deep electrodes to relieve the symptoms. With the standard high-frequency stimulation for treating Parkinson's disease, a so-called high-frequency permanent stimulation is carried out at frequencies of more than 100 Hz. This kind of treatment has no long-lasting therapeutic effects (cf. P. Temperli, J. Ghika, J.-G. Villemure, P. Burkhard, J. Bogousslaysky, and F. Vingerhoets: How do Parkinsonian signs return after discontinuation of subthalamic DBS? Neurology 60, 78 (2003)). "Coordinated reset stimulation" (CR stimulation), that can additionally have long-lasting therapeutic effects, manages with less stimulation current (P. A. Tass, L. Qin, C. Hauptmann, S. Doveros, E. Bezard, T. Boraud, W. G. Meissner: Coordinated reset neuromodulation has sustained after-effects in Parkinsonian monkeys. Annals of Neurology 72, 816-820 (2012); I. Adamchic, C. Hauptmann, U. B. Barnikol, N. Pawelcyk, O. V. Popovych, T. Barnikol, A. Silchenko, J. Volkmann, G. Deuschl, W. Meissner, M. Maarouf, V. Sturm, H.-J. Freund, P. A. Tass: Coordinated Reset Has Lasting Aftereffects in Patients with Parkinson's Disease. Movement Disorders 29, 1679 (2014)).

With other diseases, e.g. epilepsy that cannot be sufficiently treated with medication, different electrodes, e.g. epicortical or epidural electrodes, are also implanted in addition to deep electrodes. With further diseases, e.g. chronic pain syndromes, it is customary to stimulate the spinal cord not only by means of deep electrodes in the brain, but also by means of e.g. epidural electrodes. In contrast to CR stimulation, most other types of stimulation have no long-lasting therapeutic effects.

Therapeutic effects can also be achieved by direct stimulation of the brain tissue or spinal cord by light, e.g. via implanted light-guides. Different spatiotemporal stimulation patters such as CR stimulation can also be used in this respect.

Although the deep brain stimulation by means of invasive CR stimulation enables long-lasting therapeutic effects, this approach has relevant limitations:

(a) Typically, stimulation takes place intermittently, i.e. by means of a plurality of stimulation epochs, to reduce the current input. The intermittent stimulation can reduce the side-effect rate and restrict the total power consumption. Since a considerably reduced power consumption enables the use of a substantially smaller battery or of a corresponding rechargeable battery, it can be made possible in this manner to use particularly small implants that are gentle (with respect to surgical trauma and the risk of infection). The effect of the prior CR stimulation fluctuates by too much from stimulation epoch to stimulation epoch, i.e. there are too many stimulation epochs with an insufficiently pronounced effect. In other words, the stimulation effect is dependent to a relevant degree on the initial conditions of the organism or nervous system in which the stimulation is started. If e.g. a very good effect is achieved in the one stimulation epoch, this effect will rather be unsatisfactory in a next stimulation epoch. To compensate the less effective stimulation epochs, a larger number of stimulation epochs is necessary to build up a good therapeutic effect.

(b) The stimulation success depends too greatly on the stimulus intensity in the previous form of the CR stimulation. Different factors can relevantly modify the stimulus strength. The effective stimulus intensity that actually arrives at the neuronal target population can e.g. fall due to scarring around implanted deep electrodes.

(c) The stimulus strength must very generally be considered in relation to characteristic parameters of the system to be stimulated, that is of the body or of the nervous system. Since these parameters (e.g. specific ion concentrations, fluid volumes, hormone concentrations, etc.) fluctuate and are e.g. subject to pronounced fluctuations at different times of day, an optimum stimulus strength should either be correspondingly corrected or a stimulation method should be used whose stimulation effects are as independent as possible of these fluctuations.

In summary, the effect of the previously used CR stimulation is not sufficiently robust with respect to fluctuations of the stimulus intensity as well as with respect to characteristic parameters of the organism or nervous system to be stimulated (at the start of the stimulation as well as in the course of stimulation) and the effect of the CR stimulation in particular fluctuates by too much from stimulation epoch to stimulation epoch, i.e. there are too many stimulation epochs with a small effect.

SUMMARY

It is the underlying object of the invention to provide an apparatus and a method that allow improved, and in particular long-lasting, therapeutic effects to be achieved over a wide intensity range.

The object underlying the invention is satisfied by the features of the independent claims. Advantageous further developments and aspects of the invention are set forth in the dependent claims.

BRIEF DESCRIPTION OF THE DRAWINGS

The invention will be explained in more detail in the following in an exemplary manner with reference to the drawings. There are shown in these.

DETAILED DESCRIPTION

Figure 1:
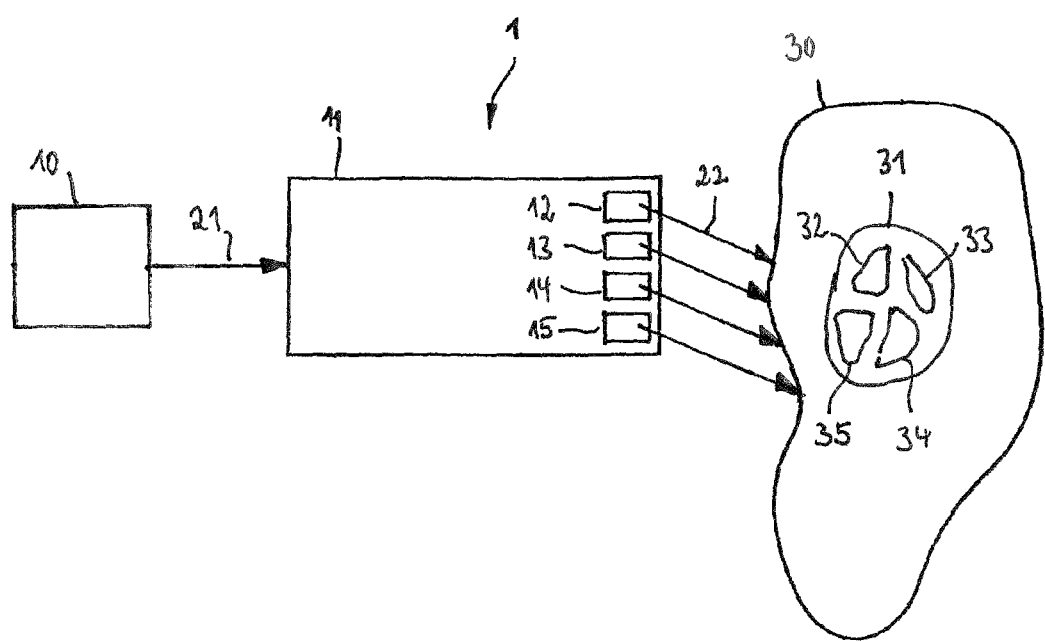
FIG. 1 illustrates a schematic representation of an apparatus for suppressing a pathologically synchronous and oscillatory neuronal activity and in particular for desynchronizing neurons having a pathologically synchronous and oscillatory activity in accordance with a first embodiment.

An apparatus 1 for stimulating neurons having a pathologically synchronous and oscillatory neuronal activity is shown schematically in FIG. 1. The apparatus 1 comprises a control unit 10 and a stimulation unit 11 that has a plurality of stimulation elements. Four stimulation elements 12, 13, 14 and 15 are shown by way of example in FIG. 1. The stimulation unit 11 can naturally, however, also have a different number of stimulation elements. In the case of electrical stimulation, the stimulation elements 12 to 15 can e.g. be stimulation contact surfaces of one or more electrodes for applying electrical stimuli. If stimulation takes place optically, light guides can e.g. be used as the stimulation elements 12 to 15 to stimulate the neuronal tissue with light stimuli at the desired points.

During the operation of the apparatus 1, the control unit 10 carries out a control of the stimulation unit 11. For this purpose, the control unit 10 generates control signals 21 which are received by the stimulation unit 11.

The stimulation unit 11 is surgically implanted in the body of the patient and on the basis of the control signals 21 generates stimuli 22, in particular electrical and/or optical stimuli 22, which are administered to the brain and/or to the spinal cord 30 of the patient. The stimuli 22 are adapted to suppress the pathologically synchronous and oscillatory neuronal activity on administration to the patient and in particular to desynchronize the neurons having the pathologically synchronous and oscillatory activity.

The control unit 10 can be a non-invasive unis, i.e. it is located outside the body of the patient during the operation of the apparatus 1 and is not surgically implanted in the body of the patient.

The apparatus 1 and the apparatus 2 described further below in connection with FIG. 3 can in particular be used for treating neurological or psychiatric diseases, e.g. Parkinson's disease, essential tremor, tremor resulting from multiple sclerosis as well as other pathological tremors, dystonia, epilepsy, depression, locomotor disorders, cerebellar diseases, obsessive compulsive disorders, dementia, Alzheimer's, Tourette's syndrome, autism, functional disorders after stroke, spasticity, tinnitus, sleep disorders, schizophrenia, irritable bowel syndrome, addiction diseases, borderline personality disorder, attention deficit syndrome, attention deficit hyperactivity syndrome, pathological gambling, neuroses, bulimia, anorexia, eating disorders, burnout syndrome, fibromyalgia, migraine, cluster headache, general headache, neuralgia, ataxia, tic disorder or hypertension as well as further diseases which are characterized by pathologically increased neuronal synchronization.

The aforesaid diseases can be caused by a disorder of the bioelectrical communication of neuronal assemblies which are connected in specific circuits. In this respect, a neuronal population continuously generates pathological neuronal activity and possibly a pathological connectivity associated therewith (network structure). In this respect, a large number of neurons synchronously form action potentials, i.e. the participating neurons fire excessively synchronously. In addition, there is the fact that the pathological neuronal population has an oscillatory neuronal activity, i.e. the neurons fire rhythmically. In the case of neurological or psychiatric diseases, the mean frequency of the pathological rhythmic activity of the affected neuronal assemblies lies approximately in the range from 1 to 30 Hz, but can also be outside this range. In healthy people, the neurons fire qualitatively differently, in contrast, e.g. in an uncorrelated manner.

The apparatus 1 is shown during a CR stimulation in FIG. 1. At least one neuronal population 31 in the brain and/or spinal cord 30 of the patient has a pathologically synchronous and oscillatory neuronal activity as described above. The stimulation unit 11 stimulates the pathologically active neuronal population 31 in the brain 29 and/or spinal cord 30 with the electrical and/or optical stimuli 22 either directly or the stimuli 22 are forwarded via the nervous system to the pathologically active neuronal population 31. The stimuli 22 are designed such that the time-delayed (or phase-shifted) stimulation by at least two stimulation elements effects a desynchronization of the pathologically synchronous activity of the neuronal population 31. A lowering of the coincidence rate of the neurons effected by the stimulation can result in a lowering of the synaptic weights and thus in an unlearning of the tendency to produce pathologically synchronous activity.

The stimuli 22 administered in the CR stimulation effect a reset of the phase of neuronal activity of the stimulated neurons in the neuronal population 30. The phase of the stimulated neurons is set to or close to a specific phase value, e.g. 0°, independently of the current phase value by the reset (it is not possible in practice to set a specific phase value exactly; however, this is also not required for a successful CR stimulation). The phase of the neuronal activity of the pathological neuronal population 31 is thus controlled by means of a direct stimulation. Since the pathological neuronal population 31 is stimulated at different points via the stimulation elements 12 to 15, the respective phases of the neuronal activity of the subpopulations 32 to 35 of the pathological neuronal population 31 shown in FIG. 1 are reset at different points in time in that the stimuli 22 are applied in a time-delayed (or phase-shifted) manner by the stimulation elements 12 to 15. As a result, the pathological neuronal population 31 whose neurons were previously active synchronously and at the same frequency and phase are split into a plurality of subpopulations having different phases. The stimulation element 12, for example, stimulates the subpopulation 32; the stimulation element 13 stimulates the subpopulation 33; the stimulation element 14 stimulates the subpopulation 34; and the stimulation element 15 stimulates the subpopulation 35. The neurons are still synchronous and also still fire at the same pathological frequency within each of the subpopulations 32 to 35; however, each of the subpopulations 32 to 35 has that phase with respect to its neuronal activity that was imparted on it by the stimulus 22 generated by the respective stimulation element 32 to 35. This means that the neuronal activities of the individual subpopulations 32 to 35 still have an approximately sinusoidal curve at the same pathological frequency, but different phases, after the resetting of their phases.

As described above, the stimulation elements 12 to 15 stimulate different subpopulations with the stimuli 22. In this respect, however, it does not necessarily have to be a case of disjunctive subpopulations, i.e. subpopulations completely separate from one another. The subpopulations stimulated by the stimulation elements 12 to 15 can also overlap one another.

Due to the pathological interaction between the neurons, the state with at least two subpopulations generated by the stimulation is unstable and the total neuronal population 31 fast approaches a state of complete desynchronization in which the neurons fire without correlation. The desired state i.e. the complete desynchronization is thus not immediately present after the time-offset (or phase-shifted) application of the phase-resetting stimuli 22, but is usually adopted within a few periods or even in less than one period of the pathological frequency.

One theory for explaining the stimulation success is based on the fact that the ultimately desired desynchronization is only made possible by the pathologically increased interaction between the neurons. In this respect, a self-organization process is made use of which is responsible for the pathological synchronization. It also has the effect that a division of an overall population 31 into subpopulations 32 to 35 with different phases is followed by a desynchronization. In contrast to this, no desynchronization would take place without a pathologically increased interaction of the neurons.

Furthermore, a reorganization of the connectivity of the disturbed neuronal networks can be achieved by the CR stimulation so that long-continuing therapeutic effects can be brought about. The obtained synaptic conversion is of great importance for the effective treatment of neurological or psychiatric diseases.

Figure 2A:
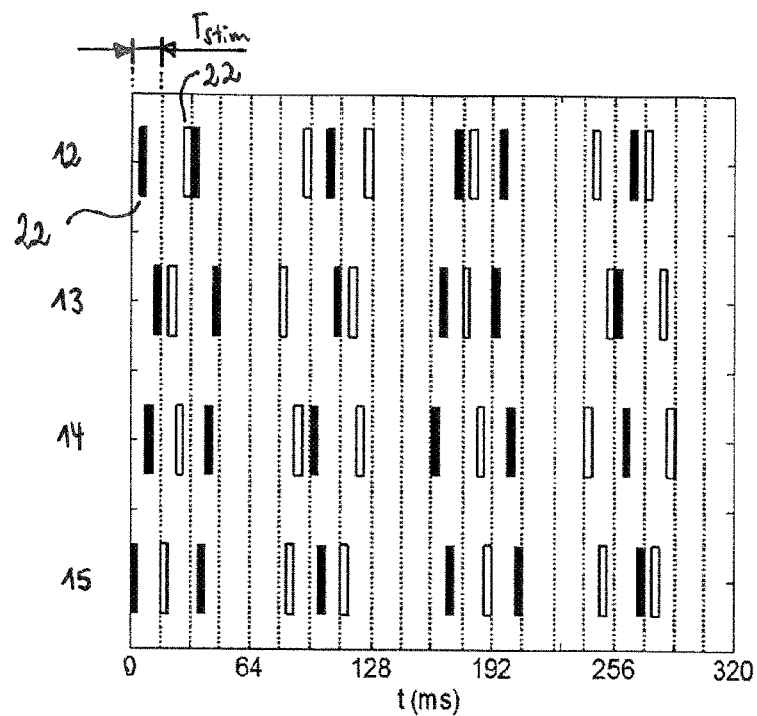
FIG. 2A illustrates a schematic representation of a CR stimulation with fast-varying stimulus sequences.

FIG. 2A shows a CR stimulation in which the four stimulation elements 12 to 15 repetitively generate sequences of stimuli 22. The stimuli 22 generated by the stimulation elements 12 to 15 are applied among one another against the time t in FIG. 2A. The sequences are generated in a predefined time pattern that comprises consecutive cycles. The individual cycle are delineated from one another by dashed lines in FIG. 2A. Each cycle has the length $T_{stim}$. In each cycle in which a stimulation takes place, the simulation elements 12 to 15 together generate exactly one sequence of stimuli 22 and each stimulation element 12 to 15 generates exactly one stimulus 22, i.e. each sequence in the present example comprises a progression of four time-delayed stimuli 22 that are in particular generated by respective different stimulation elements 12 to 15, wherein the time delay can in particular relate to the initial times of the stimuli 22. The order in which the stimulation elements 12 to 15 generate the stimuli 22 varies at the start of each cycle in the present example. A different filling of the bars shown in FIG. 2A that symbolize the stimuli 22 shows a variation of the order. The stimulation elements 12 to 15, for example, generate the stimuli 22 in the order 15-12-14-13 in the first cycle shown in FIG. 2A. The order in the second cycle is 15-13-14-12 and the order in the third cycle is 12-15-14-13.

Furthermore, in the exemplary stimulation form shown in FIG. 2A, stimuli 22 are always applied in three consecutive cycles and then a break in which no stimuli 22 are generated is observed for two cycles. This pattern is periodically repeated.

Figure 2B:
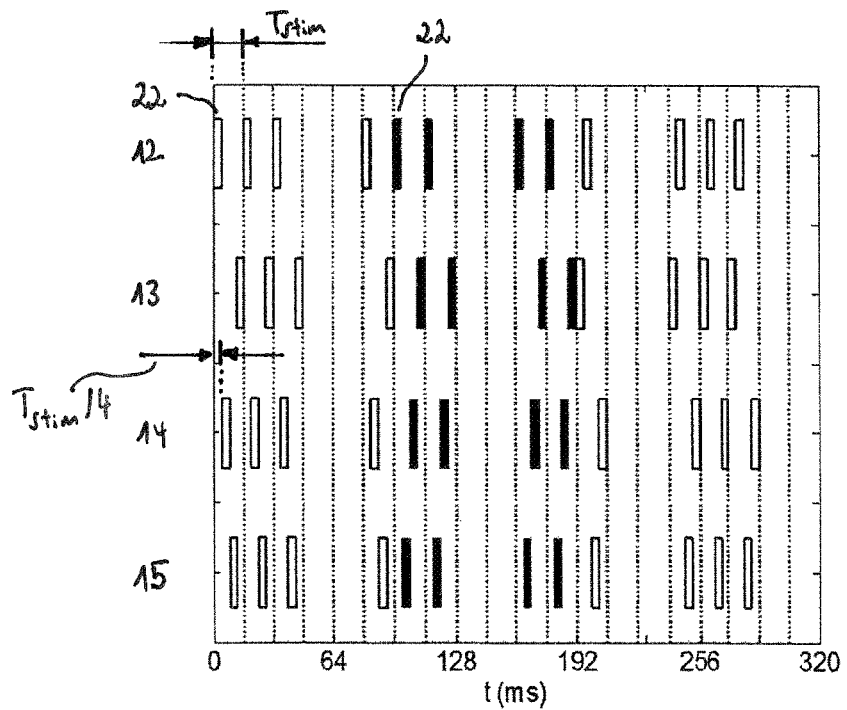
FIG. 2B illustrates a schematic representation of a CR stimulation with slowly varying stimulus sequences.

FIG. 2B shows a further development of the CR stimulation of FIG. 2A. The main difference from the stimulation in accordance with FIG. 2A is that the sequences are only varied very slowly in the CR stimulation shown in FIG. 2B. Provision is in particular made that the order in which the stimulation elements 12 to 15 generate the stimuli 22 within a sequence is kept constant for at least 20 sequences generated after one another and is only varied afterward. A CR stimulation using such slowly varying sequences is considerably superior with respect to the CR stimulation shown in FIG. 2A since its desired, i.e. therapeutic, stimulation effect (i) is more pronounced; (ii) varies much less from stimulation epoch to stimulation epoch; and (iii) is considerably more robust with respect to fluctuations of the stimulus intensity; with respect to fluctuations of characteristic parameters of the body or of the nervous system; and in particular with respect to variations of the initial values.

It is generally known that the repetition of the content to be learned plays an important role during learning. The invention utilizes the surprising relationship that the repetition is also of very high importance in the unlearning. I.e. to unlearn pathologically synchronous synaptic links and thus pathologically synchronous neuronal activity considerably better, the sequences of the CR stimulation should only be varied slowly so that every individual sequence is repeated frequently enough.

Provision can be made, as described above, that the sequences remain the same for at least 20 sequences generated after one another and are only changed afterward. It is furthermore conceivable to increase the repetition of the same sequence and to keep the order in which the stimulation elements 12 to 15 generate the stimuli 22 per sequence constant for at least 25 or at least 30 consecutively generated sequences. It must again be pointed out at this point that the sequences are already varied after fewer than 20 sequences in FIG. 2B for reasons of illustration. This is, however, only to be understood as a simplified representation of a sequence variation that is slow in comparison with FIG. 2A.

In accordance with an embodiment, only the order in which the stimulation elements 12 to 15 generate the stimuli 22 per sequence is varied in the CR stimulation shown in FIG. 2B. All the other stimulation parameters can remain constant during the CR stimulation.

The variation of the sequences can e.g. take place stochastically or deterministically or in a mixed stochastic-deterministic manner.

Exactly as in FIG. 2A, cycles can also be provided in the CR stimulation in accordance with FIG. 2B in which stimulation breaks are observed. Stimuli 22 can thus be generated during n consecutive cycles and, during the following m cycles, no stimuli 22 are generated that are designed to suppress the pathologically synchronous and oscillatory neuronal activity, where n and m are non-negative whole numbers. It is, however, conceivable that different stimuli that are not adapted to suppress pathologically synchronous and oscillatory neuronal activity are applied during the stimulation breaks, in particular using the stimulation unit 11. Provision can furthermore be made that the stimulation unit 11 does not generate any stimuli during the stimulation breaks. The pattern of n cycles with stimulation and m cycles without stimulation can be periodically continued.

Provided that provision is made to vary the sequences after a predefined number i of sequences (i≥20), in accordance with an embodiment, the cycles without any stimulation are not counted, i.e. in this embodiment, a variation of the order in which the stimulation elements 12 to 15 generate the stimuli 22 only takes place when a respective sequence of stimuli 22 was actually applied in i cycles. The number i according to which the sequence is respectively varied, can e.g. be determined in accordance with stochastic or deterministic or mixed stochastic-deterministic rules.

The variation of the sequences can furthermore take place at a constant rhythm, i.e. a variation always takes place, for example, after i cycles.

Each of the four stimulation elements 12 to 15 stimulates a respective one of the subpopulations 32 to 34 of the pathological neuronal populations 31 shown in FIG. 1. During the at least 20 cycles in which the sequences are constant, the stimulus 22 is periodically applied with the period $T_{stim}$ by each of the stimulation elements 12 to 15. The stimuli 22 effect a phase reset of the neuronal activity of the respective stimulated subpopulation. The time delay between stimuli 22 generated directly after one another in time by different stimulation elements within a sequence furthermore amounts to $T_{stim}/4$ since, in the present embodiment, four stimulation elements 12 to 15 are used for the CR stimulation. For the general case of P stimulation elements used for the stimulation, the time delay between stimuli 22 generated directly after one another in time by different stimulation elements within a sequence would amount to $T_{stim}/P$ (a deviation from this value by e.g. up to ±5%, ±10% or ±20% is also possible). The time delay $T_{stim}/P$ can relate to the initial points in time of the stimuli 22. The stimuli 22 generated by different stimulation elements can be identical except for the different starting times.

The period $T_{stim}$ that indicates the duration of a cycle, on the one hand, and the period with which unchanging sequences and the stimuli 22 generated by a respective stimulation element 12 to 15, on the other hand, can be close to the mean period of the pathological oscillation of the neuronal population 31 having the pathologically synchronous and oscillatory neuronal activity or can differ from the mean period by up to ±5%, ±10% or ±20%. The frequency $f_{stim}=1/T_{stim}$ is typically in the range from 1 to 30 Hz. The period of the pathological oscillation of the neuronal population 31 to be stimulated can be measured by means of EEG, for example. It is, however, also possible to use text book values or empirical values that relate to the respective disease to be treated for the period of the pathological oscillation.

The phase-resetting stimuli 22 can, for example, be individual stimuli or also assembled stimuli. Each stimulus 22 can, for example, comprise a pulse train of 1 to 100, in particular 2 to 10, individual pulses. The individual pulses within a pulse train are repeated without interruption at a frequency in the range from 50 to 500 Hz, in particular in the range from 100 to 150 Hz.

The stimulation unit 11 can generally include any desired number L of stimulation elements (L≥2), but all L stimulation elements do not necessarily have to be used in a stimulation; for example, only a selection of P or L stimulation elements can also generate the stimuli (2≤P≤L). With P stimulation elements, P! possible different sequences result, with each of the P stimulation elements generating exactly one stimulus 22 in each of these sequences. It is conceivable to use all P! possible sequences for the stimulation or also to select a subset for the stimulation from the set of P! possible sequences. This subset can also vary in time in accordance with stochastic or deterministic or mixed stochastic-deterministic rules. The progression of the sequences can be random or can be fixed before or also during the stimulation.

The apparatus 1 shown in FIG. 1 for stimulating neurons having a pathologically synchronous and oscillatory neuronal activity carries out a so-called "open-loop" stimulation, i.e. a stimulation without sensors that are used for feedback and/or for control of the stimulation.

Figure 3:
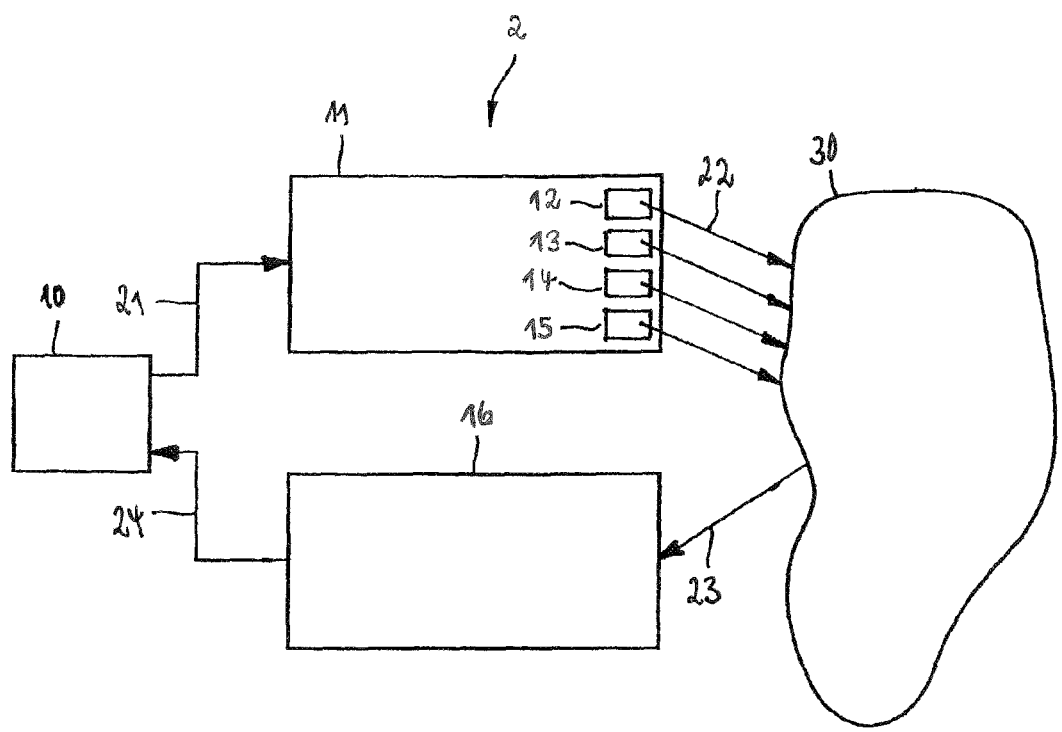
FIG. 3 illustrates a schematic representation of an apparatus for suppressing a pathologically synchronous and oscillatory neuronal activity and in particular for desynchronizing neurons having a pathologically synchronous and oscillatory activity in accordance with a second embodiment.

FIG. 3 schematically shows an apparatus 2 for stimulating neurons having a pathologically synchronous and oscillatory neuronal activity with which a closed-loop stimulation can be carried out. The apparatus 2 is a further development of the apparatus 1 shown in FIG. 1 and, exactly like the apparatus 1, includes a control unit 10 and an implantable stimulation unit 11 that have the same functions as the above-described control and stimulation units 10, 11 of the apparatus 1.

The apparatus 2 furthermore comprises a measuring unit 16. The stimulation effect achieved by the stimuli 22 is monitored with the aid of the measuring unit 16. The measuring unit 16 records one or more measured signals 23 measured at the patient, converts them as required into electrical signals 24 and supplies them to the control unit 10. The neuronal activity in the stimulated target zone or in a zone associated with the target zone can in particular be measured by means of the measuring unit 16, with the neuronal activity of this zone correlating sufficiently closely with the neural activity of the target zone. A non-neuronal activity, e.g. a muscular activity, or the activation of the autonomous nervous system can also be measured by means of the measuring unit 16 provided that they are sufficiently closely correlated with the neuronal activity of the target region.

The measuring unit 16 includes one or more sensors that in particular make it possible to demonstrate a decrease or increase in the amplitude of the pathological oscillatory activity.

Non-invasive sensors can be used as the sensors, e.g. chronically or intermittently used electroencephalography (EEG) electrodes or electromyography (EMG) electrodes or magnetoencephalography (MEG) sensors. The neuronal activity can also be determined by detection of characteristic movement patterns such as tremor, akinesia, or epileptic fits with the aid of an accelerometer or gyroscope or indirectly by measuring the activation of the autonomous nervous system by means of a measurement of the skin resistance. Mental state values that can be input into portable devices, e.g. smartphones, by the patient can also be used to monitor the stimulation success.

Alternatively, the sensors can be implanted in the body of the patient. Epicortical electrodes, deep brain electrodes for the measurement of e.g. local field potentials, subdural or epidural brain electrodes, subcutaneous EEG electrodes and subdural or epidural spinal cord electrodes can, for example, serve as invasive sensors. The deep electrodes for measuring the local field potentials can also be combined construction-wise or can even be identical to the deep electrodes used for the stimulation.

The control unit 10 processes the signals 24, e.g. the signals 24 can be amplified and/or filtered, and analyzes the processed signals 24. The control unit 10 checks the stimulation success using the measured signals recorded in response to the application of the stimuli 22.

In accordance with an embodiment, the sequences generated by the stimulation unit are varied with a constant rhythm, i.e. the order in which the stimulation elements 12 to 15 generate the stimuli per sequence is kept constant for a predefined number of cycles (at least 20) and the order is varied afterward. The order is subsequently again kept constant for the predefined number of cycles and is varied afterward. This pattern is correspondingly continued. In this embodiment, the rhythm with which the sequences are varied remains constant is in particular not adapted to the measured signals 23 processed by the control unit 10; however, other stimulation parameters such as the amplitude of the pulse trains applied as stimuli 22 can be set in dependence on the measured signals 23.

The above embodiment can be further developed in that the stimulation parameters are set in dependence on the processed measured signals 23. The control unit 10 checks the stimulation success using the measured signals recorded in response to the application of the stimuli 22 and sets the stimulation parameters, in particular the rhythm with which the stimulation sequences are varied, in dependence on the stimulation success.

The stimulation success can in particular be checked by means of a threshold value comparison. Depending on which signals are used for determining the stimulation success, different threshold value comparisons result. If e.g. the pathologically neuronal synchronization is measured via the sensors of the measuring unit 16, e.g. EEG electrodes or deep electrodes (as an LFP signal), experience has shown that the lowering of the synchronization by e.g. at least 20% in comparison with the situation without stimulation is sufficient to determine a sufficient stimulation success. In accordance with an embodiment, an insufficient stimulation success can be determined if the pathologically neuronal synchronization by the application of the stimuli 22 is not reduced by at least a predefined value. If symptoms of the patient are used for determining the stimulation success, which reduction is to be considered as a clinically relevant improvement depends on the kind of clinical parameters used. Such reduction values (e.g. in the sense of the so-called minimal clinically perceptible improvement) are familiar to the skilled person.

If the CR stimulation in accordance with a threshold comparison is not sufficiently effective, i.e. a disease-specific marker does not reduce by a predefined threshold value in comparison with the balance state or with a starting/initial value, the number of repetitions of the same sequence is extended. If the stimulation is in contrast successful in accordance with the threshold value criterion, the number of repetitions of the same sequence is shortened. In the simplest case, this can be a binary switching between two values of the number of repetitions of the same sequence: e.g. 25 repetitions with a successful stimulation; in contrast, e.g. 100 repetitions with an unsuccessful stimulation. The demand-controlled number of repetitions of the same sequence can, however, also be varied/parameterized in smaller steps.

The individual components of the apparatus 1 and 2, in particular the control unit 10, the stimulation unit 11 and/or the measuring unit 16, can be separate from one another in a construction aspect. The apparatus 1 and 2 can therefore also be understood as systems. The control unit 10 can therefore include a processor, e.g. a microcontroller, for carrying out its work. The stimulation processes described herein can be stored as software code in a memory associated with the control unit 10.

The stimulation unit 11 can e.g. be a brain pacemaker and in this case has one or more implantable electrodes, e.g. deep electrodes, as well as optionally connection cables connected therebetween. The electrodes of the stimulation unit 11 typically comprise an insulated electrode shaft and a plurality of stimulation contact surfaces which have been introduced into the electrode shaft.

Figure 4:
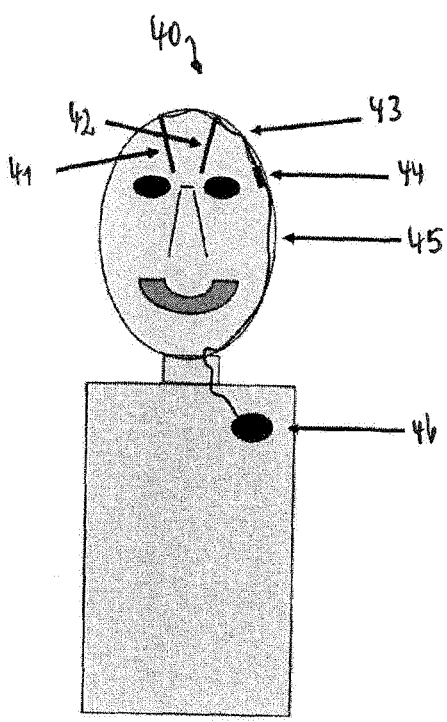
FIG. 4 illustrates a schematic illustration of an apparatus for the electrical stimulation of neurons having a pathologically synchronous and oscillatory neuronal activity.

FIG. 4 schematically shows an apparatus 40 for invasive electrical stimulation of neurons having a pathologically synchronous and oscillatory neuronal activity in accordance with an embodiment of the invention. The apparatus 40 comprises two electrodes 41, 42 that are implanted in the brain of the patient and are connected to a connector 44 via cable 43. The connector 44 is in turn connected to a control unit 46 via a cable 45. The apparatus 40 can have the functions of the above-described apparatus 1 and 2.

Implantable stimulation units for the optical stimulation of neuronal tissue are known. For example a light source such as a laser, a laser diode or an LED can generate a light beam that is distributed with the help of a light coupling to the inputs of a fiber bundle comprising a plurality of light guides. In this process, a control unit predefines e.g. the point in time at which an individual light pulse or a series of light pulses is coupled into which fiber of the fiber bundle. The decoupling points of the individual fibers of the fiber bundle, i.e. the ends of the fibers, lie at different points in the target region in the brain or spinal cord of the patient. The light thus stimulates different sites of the target region in a time progression predefined by the control unit. Different implantable stimulation units can, however, also be used that are suitable for a direct optical stimulation of neuronal tissue.

As described above, the stimuli 22 effect a reset of the phase of the neuronal activity of the stimulated neurons in the CR stimulation. The phase reset of the individual stimuli 22 can be checked with the aid of the measured signals 23 recorded by the measuring unit 16. Such an examination can be carried out before the actual therapeutic neurostimulation.

For this purpose, a signal that sufficiently represents the activity of the subpopulation stimulated over the jth stimulation channel is measured via a sensor of the measuring unit 16. A stimulation channel can be represented by a stimulation element, e.g. by one of the stimulation elements 12 to 15 that stimulates a specific subpopulation. The above signal is obtained either directly from the subpopulation via a non-invasive measurement, e.g. via EEG or MEG electrodes, or via an invasive measurement, e.g. via implanted electrodes, as a surface EEG or as a local field potential via deep electrodes. The signal can also be determined indirectly via the measurement of a value correlated with the activity of the stimulated subpopulation. EEG/MEG/LFP signals of the neuronal activity of another neuronal population closely coupled to this subpopulation are suitable for this purpose or associated electromyography signals, accelerometer signals or gyroscope signals.

Since neuronal signals typically include rhythmic activity in different frequency bands, it is advantageous in such cases to determine the signal $x_j(t)$ that represents the pathological oscillatory activity of the subpopulation stimulated by the jth stimulation channel, e.g. by means of band pass filtering or wavelet analysis or empirical mode decomposition.

A procedure that is only a little complex to check a phase reset comprises determining the averaged stimulus response. A stimulus having identical stimulus parameters is applied at the times $\tau_1, \tau_2, \ldots, \tau_1$ for this purpose. The intervals between the individual stimuli $\tau_{k+1}-\tau_k$ should be sufficiently large and randomized, that is should not be constant, in order to avoid transient effects (cf. P. A. Tass: Transmission of stimulus-locked responses in two coupled phase oscillators. Phys. Rev. E 69, 051909-1-24 (2004)). The intervals $\tau_{k+1}-\tau_k$ should typically be in the range of at least tenfold, preferably a hundredfold of the mean period of the pathological oscillation. The stimulus response averaged over all 1 test stimuli is calculated in accordance with the following equation:

$$\bar{x}_j(t) = \frac{1}{l}\sum_{k=1}^{l} x_j(\tau_k + t) \quad (1)$$

Provided that the intervals $\tau_{k+1}-\tau_k$ between the individual stimuli are sufficiently large, no averaged stimulus response is obtained in the pre-stimulus range, i.e. in the range before the application of a respective stimulus (cf. P A. Tass: Transmission of stimulus-locked responses in two coupled phase oscillators. Phys. Rev. E 69, 051909-1-24 (2004)). A phase reset can be determined when an averaged stimulus response can be detected, i.e. when a stimulus response different from zero is found in the post-stimulus range, i.e. in the range for t>0, where t=0 represents the starting time of the respective stimulus. This can be determined by a visual inspection. It can also be carried out by the apparatus 2, in particular by the control unit 10, in that the pre-stimulus distribution of $\bar{x}_j(t)$ or $|\bar{x}_j(t)|$ is observed and a characteristic threshold value is determined, e.g. the 99th percentile of the pre-stimulus distribution of $|\bar{x}_j(t)|$ or simply its maximum. If now e.g. the amount of the post-stimulus response exceeds this characteristic threshold value in principle or for a predefined minimum time, e.g. 20 ms, an averaged response different from zero is present. A phase reset can be present in this case. I.e. the stimulus strength would have to be increased for so long until the post-stimulus response differs from a zero line. In addition to the method presented here that is simple, but has been proven in practice, other statistical tests known to the skilled person can be used for the signal analysis.

A more exact, but more complex, variant for investigating whether the stimuli effect a phase reset is offered by the analysis of the phase. The phase $\psi_j(t)$ of $x_j(t)$ is determined for this purpose. This is done by means of a Hilbert transformation from the signal that represents the pathological oscillatory activity that is determined by means of band pass filtering or empirical mode decomposition. The empirical mode decomposition allows, in contrast to band pass filtering, a parameter-independent determination of physiologically relevant modes in different frequency ranges (cf. N. E. Huang et al.: The empirical mode decomposition and the Hilbert spectrum for nonlinear and non-stationary time series analysis. Proc. R. Soc. A: Math. Phys. Eng. Sci. 454:903-995 (1998)). The combination of empirical mode decomposition with a subsequent Hilbert transformation is called a Hilbert-Huang transformation (cf. N. E. Huang et al.: A confidence limit for the empirical mode decomposition and Hilbert spectral analysis, Proceedings of the Royal Society of London Series A, 459, 2317-2345 (2003)). The phase $\psi_j(t)$ can also be determined by means of wavelet analysis.

A phase reset is present when the phase $\psi_j(t)$ is set to a preferred value by a stimulus (at a stimulus start at t=0) after a specific time. I.e. $\{\psi_j(\tau_k+t)\}_{k=1,\ldots,l}$, the distribution of the values of the phase $\psi_j(t)$ acquired from the 1 stimulus responses has an accumulation point at the time t (relative to the burst start at t=0). The skilled person is aware of different methods with which it can be demonstrated that a distribution has an accumulation value (that is a peak). A common method is the determination of the phase reset index $\rho(t)$ by means of a circular mean value.

$$\rho(t) = \left| \frac{1}{l}\sum_{k=1}^{l} \exp[i\psi_j(\tau_k + t)] \right| \quad (2)$$

A phase reset is present when $\rho(t)$ e.g. exceeds the maximum or the 99th percentile of the pre-stimulus distribution of $\rho(t)$ (at a point in time or within a small time window of e.g. 20 ms width).

The analysis using the averaged responses $\bar{x}_j(t)$ has proved itself sufficiently in practice.

The effects achievable using the invention described herein are illustrated with reference to simulation results in FIGS. 5 to 7. The simulation is based on a network of 200 neurons, wherein all the neurons have a highly exciting short-range coupling and a weak inhibitory long-range coupling among one another. The synaptic coupling strengths in the network can change in accordance with STPD (spike timing dependent plasticity) rules. An initially strongly coupled network produces highly synchronous neuronal activity.

The simulation is based on the following conditions. The CR stimulation starts at t=0 s and ends at t=64 s. Each cycle lasts 16 ms. A pattern of 3 cycles with stimulation and 2 cycles without stimulation is periodically repeated. The activity of the network is examined up to t=128 s, i.e. until 64 s after the end of the stimulation. The degree of synchronization S can be in the range from 0 (for a complete desynchronization) up to 1 (for a complete phase synchronization).

Figure 5A:
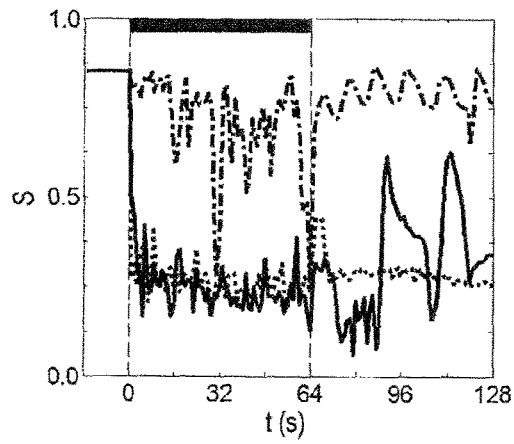
FIGS. 5A to 5B, 6A to 6D and 7A to 7B illustrate diagrams with stimulation results for fast-varying and slowly varying CR stimulations.
Figure 5B:
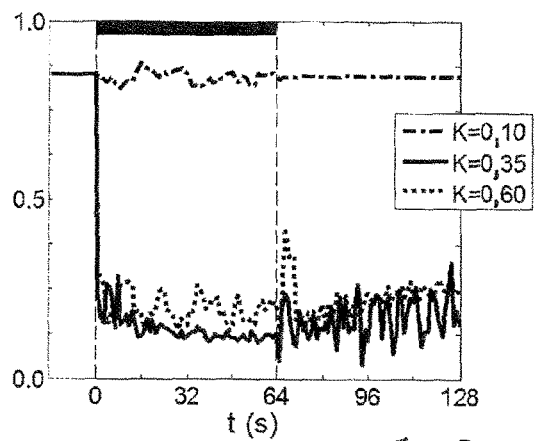

The degree of synchronization S of the simulated neuronal population having a pathologically synchronous and oscillatory neuronal activity before, during and after a CR stimulation is shown in FIGS. 5A and 5B. The horizontal bars drawn at the top in the two illustrations indicate the time period in which the CR stimulation is applied. In the simulation shown in FIG. 5A, the sequences were varied at the start of each cycle, while the sequences in the simulation shown in FIG. 5B were only varied after a respective 100 cycles. The degree of synchronization S was calculated after every millisecond. The respective 50th percentile of the values for the degree of synchronization S is shown for three different stimulation strengths K in FIGS. 5A and 5B.

It can be seen as the result from FIGS. 5A and 5B that, with the exception of the CR stimulation with a stimulation strength K of 0.10, the slowly varying CR stimulation shown in FIG. 5B shows a larger and also longer-lasting stimulation success.

Figure 6A:
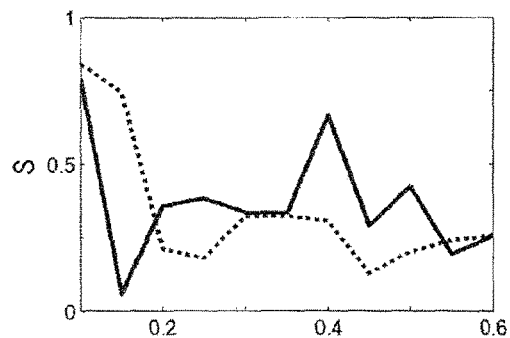

In addition to the stimulation strength K, the order of the sequences and the initial conditions of the network also have an influence on the stimulation success. This is shown in FIGS. 6A to 6D in which the degree of synchronization S is entered against the stimulation strength K. The simulations shown in FIGS. 6A and 6C are based on a variation of the sequences in each cycle, whereas the sequences were only varied after 100 cycles in the simulations shown in FIGS. 6B and 6D.

Figure 6B:
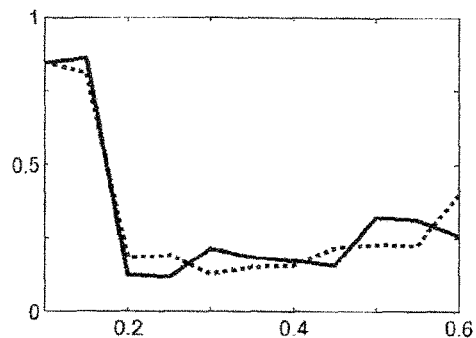
Figure 6C:
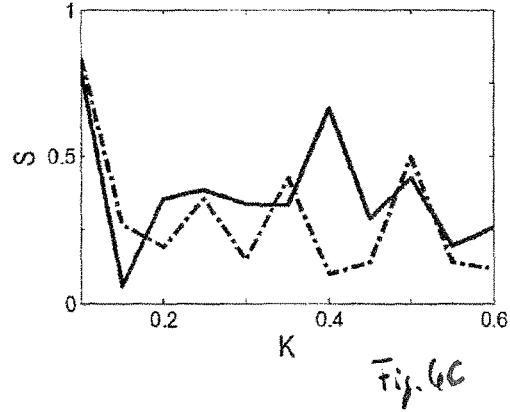

The respective 50th percentile of the values for the degree of synchronization S for the last 16 seconds of the stimulation is shown in FIGS. 6A and 6B as a function of the stimulation strength K for two different orders of the sequences. The solid lines show the simulation results for the same order of the sequences such as also formed the basis for the simulations of FIGS. 5A and 5B, while the dotted lines represent the simulation results for another order. FIGS. 6A and 6B show that the slowly varying CR stimulation is more robust with respect to the order of the sequences in comparison with the fast-varying CR stimulation.

Figure 6D:
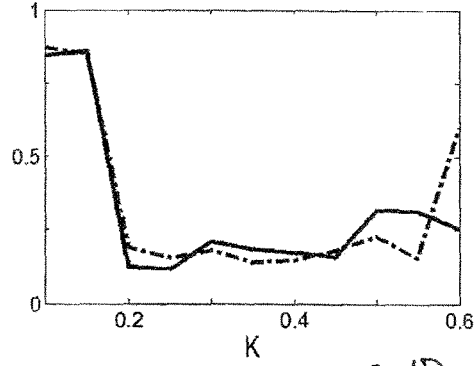

The simulations furthermore show that the starting conditions of the network also have an influence on the desynchronization of the neuronal activity. The respective 50th percentile of the values for the degree of synchronization S for the last 16 seconds of the stimulation is shown in FIGS. 6C and 6D as a function of the stimulation strength K for two different starting conditions of the sequences. The solid lines show the simulation results for the same starting conditions of the network as also formed the basis of the simulations of FIGS. 5A and 5B, while the chain-dotted lines show the simulation results for different starting conditions. The slowly varying CR stimulation also proves to be more robust with respect to the starting conditions of the network in comparison with the fast-varying CR stimulation.

Figure 7A:
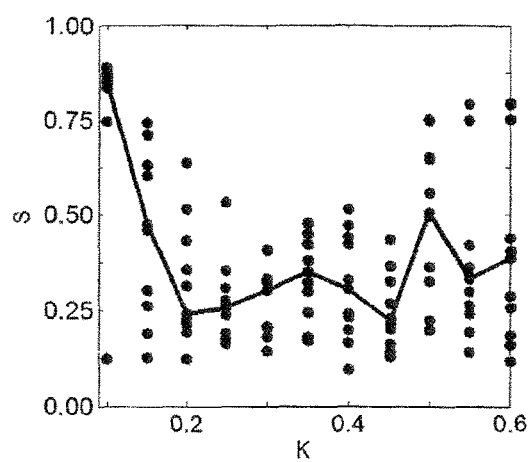
Figure 7B:
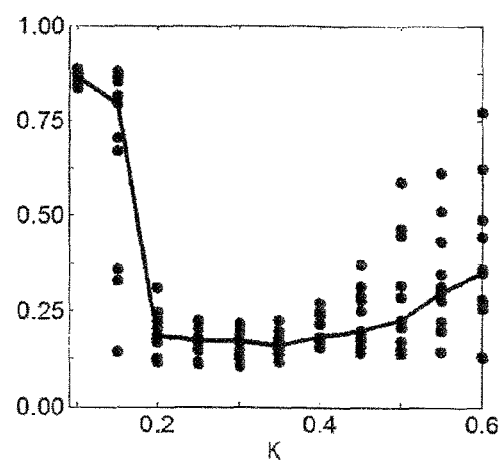

10 further simulations were carried out with different orders of the sequences and with different starting conditions of the network both for the fast-varying CR stimulation and the slowly varying CR stimulation. The results of these simulations are shown in FIGS. 7A and 7B in which the 50th percentile of the values for the degree of synchronization S for the last 16 seconds of the stimulation is entered as a function of the stimulation strength K for different orders of the sequences and for different starting conditions of the network. The median of the results for each value of the stimulation strength K is connected by a line in each case. FIG. 7A shows the results of the fast-varying CR stimulation and FIG. 7B shows the results of the slowly varying CR stimulation. It can be seen as the result from FIGS. 7A and 7B that the slowly varying CR stimulation desynchronizes the highly synchronous network more and more robustly than is possible with the fast-varying CR stimulation.

The invention claimed is:

1. An apparatus for stimulating neurons, the apparatus comprising:
   a stimulation unit implantable into a patient and having a plurality of stimulation elements for stimulating neurons in at least one of a brain and a spinal cord of the patient with stimuli; and
   a control unit configured to control the stimulation unit such that the plurality of stimulation elements repetitively generate sequences of the stimuli,
   wherein an order in which the plurality of stimulation elements generate the stimuli within each sequence is kept constant for at least 20 sequences generated after one another and is varied after the at least 20 sequences.

2. The apparatus in accordance with claim 1, wherein the sequences are generated in a time pattern that comprises consecutive cycles, and wherein a respective sequence of stimuli is generated in at least a portion of the consecutive cycles.

3. The apparatus in accordance with claim 2, wherein either exactly one sequence of stimuli is generated or no stimuli are generated within a respective cycle.

4. The apparatus in accordance with claim 2,
   wherein the stimuli are generated during n consecutive cycles and no stimuli are generated during m cycles following the n consecutive cycles; and
   wherein a pattern of the n consecutive cycles and following m cycles is periodically continued, wherein n and m are non-negative whole numbers.

5. The apparatus in accordance with claim 1, wherein a pattern according to which the order of the plurality of stimulation elements generate the stimuli within a sequence that is kept constant for at least 20 consecutively generated sequences after one another and is varied after the at least 20 sequences is repeated a plurality of times.

6. The apparatus in accordance with claim 1, wherein the stimuli are configured to suppress a pathologically synchronous and oscillatory activity of neurons on an administration to the patient over the plurality of stimulation elements.

7. The apparatus in accordance with claim 6, wherein a duration of a cycle substantially corresponds to a mean period of a pathological oscillation of the neurons.

8. The apparatus in accordance with claim 6, wherein the stimuli generated by the plurality of stimulation elements reset phases of neuronal activity of a plurality of subpopulations of the stimulated neurons having the pathologically synchronous and oscillatory activity at different points in time.

9. The apparatus in accordance with claim 1, wherein the stimulation unit includes L stimulation elements and P of the L stimulation elements generate stimuli in a respective sequence of stimuli, where $L \geq 2$ and $2 \leq P \leq L$.

10. The apparatus in accordance with claim 9, wherein each of the P stimulation elements generates exactly one stimulus within a respective sequence of stimuli.

11. The apparatus in accordance with claim 10, wherein exactly one stimulus is exactly one electrical or optical pulse train.

12. The apparatus in accordance with claim 1, further comprising a measuring unit configured to record measured signals that reproduce a neuronal activity of the neurons stimulated by the stimuli.

13. The apparatus in accordance with claim 12, wherein the control unit is further configured to extend a number of the consecutively generated sequences in which the order of the plurality of stimulation elements in which the stimuli are generated within a sequence is constant when the control unit determines based on the measured signals that a degree of synchronization of the stimulated neurons is not reduced by at least one predefined threshold value by application of the stimuli.

14. The apparatus in accordance with claim 1, wherein the stimuli are at least one of electrical stimuli and optical stimuli.

15. A method of stimulating neurons comprising:
   generating, by a stimulation unit implanted in a patient, stimuli by a plurality of stimulation elements, wherein the stimuli stimulate neurons in at least one of brain and a spinal cord of the patient;

repetitively generating, by the stimulation unit, sequences of the stimuli;

maintaining an order of the plurality of stimulation elements in which the stimuli are generated within in sequence as constant for at least 20 sequences generated after one another; and varying the order after the at least 20 sequences.

16. The method in accordance with claim 15, further comprising recording measured signals that reproduce a neuronal activity of the neurons stimulated by the stimuli.

17. The method in accordance with claim 16, further comprising extending a number of the consecutively generated sequences in which the order of the plurality of stimulation elements in which the stimuli are generated within sequence is constant when, based on the measured signals, a degree of synchronization of the stimulated neurons is not reduced by at least one predefined threshold value by application of the stimuli.

18. A computer program product for execution in a data processing system, the computer program product including instructions for:

generating, by a stimulation unit implanted in a patient, stimuli by a plurality of stimulation elements, wherein the stimuli stimulate neurons in at least one of brain and a spinal cord of the patient;

repetitively generating, by the stimulation unit, sequences of the stimuli;

maintaining an order of the plurality of stimulation elements in which the stimuli are generated within in sequence as constant for at least 20 sequences generated after one another; and varying the order after the at least 20 sequences.

19. The computer program product in accordance with claim 18, further including instructions for recording measured signals that reproduce a neuronal activity of the neurons stimulated by the stimuli.

20. The computer program product in accordance with claim 19, further including instructions for extending a number of the consecutively generated sequences in which the order of the plurality of stimulation elements in which the stimuli are generated within sequence is constant when, based on the measured signals, a degree of synchronization of the stimulated neurons is not reduced by at least one predefined threshold value by application of the stimuli.

* * * * *